United States Patent
Lin et al.

(10) Patent No.: US 10,578,575 B2
(45) Date of Patent: Mar. 3, 2020

(54) NOISE-REDUCED CAPACITIVE SENSING UNIT

(71) Applicant: SunASIC Technologies, Inc., New Taipei (TW)

(72) Inventors: Chi-Chou Lin, New Taipei (TW); Zheng-Ping He, Taipei (TW)

(73) Assignee: SunASIC Technologies, Inc., New Taipei (TW)

(*) Notice: Subject to any disclaimer, the term of this patent is extended or adjusted under 35 U.S.C. 154(b) by 226 days.

(21) Appl. No.: 15/702,814

(22) Filed: Sep. 13, 2017

(65) Prior Publication Data
US 2018/0074004 A1    Mar. 15, 2018

Related U.S. Application Data

(60) Provisional application No. 62/394,240, filed on Sep. 14, 2016.

(51) Int. Cl.
| | |
|---|---|
| G01N 27/22 | (2006.01) |
| G01R 27/26 | (2006.01) |
| G06F 3/041 | (2006.01) |
| G06F 3/044 | (2006.01) |
| G06K 9/00 | (2006.01) |

(52) U.S. Cl.
CPC .......... *G01N 27/228* (2013.01); *G06F 3/044* (2013.01); *G06F 3/0418* (2013.01); *G06K 9/0002* (2013.01)

(58) Field of Classification Search
CPC ..... G01N 27/228; G06F 3/044; G06F 3/0418; G06K 9/0002; G06K 9/0008; G06K 9/00
See application file for complete search history.

(56) References Cited

U.S. PATENT DOCUMENTS

| | | | | |
|---|---|---|---|---|
| 5,343,766 | A * | 9/1994 | Lee | G01D 5/2417 73/514.18 |
| 6,151,967 | A * | 11/2000 | McIntosh | B81B 3/0086 361/283.4 |
| 9,151,792 | B1 * | 10/2015 | Kremin | G01R 27/2605 |
| 2014/0362037 | A1 * | 12/2014 | Kao | G06F 3/042 345/174 |
| 2016/0180619 | A1 * | 6/2016 | Riedijk | G07C 9/00158 324/679 |
| 2016/0216800 | A1 * | 7/2016 | Cho | G06F 3/044 |
| 2018/0349664 | A1 * | 12/2018 | Lin | G06K 9/0002 |

\* cited by examiner

*Primary Examiner* — Christopher P McAndrew
*Assistant Examiner* — Zannatul Ferdous
(74) *Attorney, Agent, or Firm* — Jackson IPG PLLC; Demian K. Jackson (57) ABSTRACT

A noise-reduced capacitive sensing unit is disclosed. The noise-reduced capacitive sensing unit includes: a sensing plate; a first bias voltage source for providing a first bias voltage; a second bias voltage source for providing a second bias voltage; a switch unit, connected between two bias voltage sources and the sensing plate, for selectively providing one of the bias voltages to the sensing plate; an excitation signal source for providing a bi-level waveform; a reference capacitor, formed between the excitation signal source and the sensing plate, for injecting the excitation signal to the sensing plate; and a voltage follower for providing sensing results, wherein an input node of the voltage follower is connected to the sensing plate.

8 Claims, 6 Drawing Sheets

NOISE-REDUCED CAPACITIVE SENSING UNIT

FIELD OF THE INVENTION

The present invention relates to a capacitive sensing unit. More particularly, the present invention relates to a capacitive sensing unit with noise reduction feature.

BACKGROUND OF THE INVENTION

There are many human physiological characteristics which can be used to provide personnel identification for security purposes, such as fingerprint, retina, iris, DNA, or even facial features. For all the devices that are capable of distinguishing some physiological characteristics of one person from others', a fingerprint reader has the lowest cost and complexity, while the identification results are generally pretty good. In addition, the size of data required to store the minutiae of one fingerprint is small (ranging from 120 bytes to 2K bytes). This makes fingerprint identification devices widely accepted in many applications.

There are also many types of sensing techniques for capturing fingerprints. The popular ones are the optical type and capacitive type. Optical fingerprint sensing modules utilize reflected light intensity from the surface of a finger to tell where the ridges and valleys are on the contact portion of the finger. The advantage of the optical technique is reliability and low cost. However, due to the size of the embedded optical lens, the form factor of an optical fingerprint sensing module cannot be kept small. It is difficult for the optical type sensor to be embedded in portable devices. The capacitive-type fingerprint identification modules, on the other hand, are made out of silicon chips and can be made very compact. In some cases, when a fingerprint image can be fetched by slide scanning, the fingerprint sensor can be even thin and slim, too. The small form factor of capacitive-type fingerprint identification module makes it suitable for portable applications such as access control badges, bank cards, cellular phones, tablet computers, USB dongles, etc.

Capacitive-type fingerprint sensors are based on the principle that the capacitance of two parallel conductive plates is inversely proportional to the distance between them. A capacitive image sensor consists of an array of sensing units. Each sensing unit contains a sensing electrode. By using the sensing electrode as one plate of the two-plated capacitor and a dermal tissue as another plate, ridges and valleys of a fingerprint can be located by measuring the different capacitances. There are many prior arts related to the capacitive-type fingerprint identification module. Most of them have been applied to manufacture fingerprint sensors. However, there are also many problems pending for solutions. One of them is the accuracy of the sensing elements.

Due to the high-density nature, the popular capacitive image sensors are mainly manufactured with semiconductor processes. U.S. Pat. No. 7,864,992 discloses a capacitive fingerprint sensing device in which a driving signal is injected into the finger by feeding a conductive drive structure surrounding the sensor array and measuring the resulting change of the charge carried by the sensing structures in the sensor array. Although the fingerprint sensing system according to U.S. Pat. No. 7,864,992 provides an excellent combination of fingerprint image quality and sensor protection, it would, in some applications be desirable to be able to acquire a high-quality fingerprint image without the use of a separate conductive drive structure. Therefore, an innovative capacitive sensing unit with noise-reduced feature and an innovative capacitive image sensor with the capacitive sensing units are desirable.

SUMMARY OF THE INVENTION

This paragraph extracts and compiles some features of the present invention; other features will be disclosed in the follow-up paragraphs. It is intended to cover various modifications and similar arrangements included within the spirit and scope of the appended claims.

In order to fulfill the requirements mentioned above, a noise-reduced capacitive sensing unit is disclosed. The noise-reduced capacitive sensing unit includes: a sensing plate; a first bias voltage source for providing a first bias voltage; a second bias voltage source for providing a second bias voltage; a switch unit, connected between two bias voltage sources and the sensing plate, for selectively providing one of the bias voltages to the sensing plate; an excitation signal source, for providing an excitation signal with a bi-level waveform; a reference capacitor, formed between the excitation signal source and the sensing plate, for injecting the excitation signal to the sensing plate; and a voltage follower for providing sensing results, wherein an input node of the voltage follower is connected to the sensing plate. The first bias voltage is provided to the sensing plate during a first resetting stage. The second bias voltage is provided to the sensing plate during a second resetting stage. Both of the first and second bias voltages are removed during sensing stages. A first voltage shift is provided by the excitation signal source to the sensing plate through the reference capacitor during a first sensing stage. A second voltage shift is provided by the excitation signal source to the sensing plate through the reference capacitor during a second sensing stage. A noise-reduced value of the capacitive sensing unit is obtained by calculating a voltage difference between the first sensing stage and the second sensing stage.

The noise-reduced capacitive sensing unit further includes a sample-and-hold circuit for capturing and retaining an input voltage signal. The sample-and-hold circuit includes: a first charge holding capacitor, for capturing and retaining a first output electric potential, wherein one node of the first charge holding capacitor is connected to the ground; a second charge holding capacitor, for capturing and retaining a second output electric potential, wherein one node of the second charge holding capacitor is connected to the ground; and a selecting switch for choosing the output target between the first and second charge holding capacitors.

The noise-reduced capacitive sensing unit further includes a signal conditioning circuit, for amplifying a voltage difference between the first output electric potential and second output electric potential. The signal conditioning circuit includes: a differential amplifier, having a first input node connected to the first charge holding capacitor, and a second input node connected to the second charge holding capacitor, for producing a voltage output that is proportional to the difference between the first output electric potential and second output electric potential.

The signal conditioning circuit further includes an analog-to-digital converter, having an input node connected to an output node of the differential amplifier, for digitizing an output voltage of the differential amplifier and producing a binary value that represents a level of the output voltage.

Preferably, the noise-reduced capacitive sensing unit further includes a control and TO circuit, for handling the operation sequence and data input/output of a capacitive image sensor using the capacitive sensing units. The control and TO circuit comprises: a control and timing logic, for controlling all switches of the capacitive sensing unit; and buffer and TO unit, connected to an output node of the analog-to-digital converter, for receiving the output data of the analog-to-digital converter, and store the data into a buffer and then send out the data at a proper time.

Preferably, the switch unit may include: a first bias voltage switch for selectively providing the first bias voltage from the first bias voltage source to the sensing plate; and a second bias voltage switch for selectively providing the second bias voltage from the second bias voltage source to the sensing plate.

A capacitive image sensor including a number of noise-reduced capacitive sensing units above is also provided by the present invention. A method for operating the capacitive sensing unit in the capacitive image sensor includes the steps of: a) setting the excitation signal source to a high potential, and charging the sensing plate to the first bias voltage; b) stopping the first bias voltage supply to leave the sensing plate floating; c) setting the excitation signal source to a low potential; d) retaining a first output electric potential; e) keeping the excitation signal source at the low potential, and charging the sensing plate to the second bias voltage; f) stopping the second bias voltage supply to leave the sensing plate floating; g) setting the excitation signal source to the high potential; h) retaining a second output electric potential; and i) producing an output proportional to the difference between the first output electric potential and the second output electric potential by the differential amplifier.

Another capacitive image sensor including a number of noise-reduced capacitive sensing units above is also provided by the present invention. A method for operating a capacitive image sensor including the capacitive sensing units includes the steps of: a) sequentially collecting the noise-reduced values obtained under corresponding positive waveform and negative waveform for each pixel; b) converting the noise-reduced values into digitized noise-reduced values; and c) mapping the digitized noise-reduced values to corresponding locations of capacitive sensing units.

A method for operating the capacitive sensing unit includes the steps of: a) turning off all switches; b) setting the excitation signal source to a high potential, and turning on the first bias voltage switch; c) turning off the first bias voltage switch to leave the sensing plate floating; d) setting the excitation signal source to a low potential; e) charging the first charge holding capacitor to a first output electric potential; f) retaining the first output electric potential by the first charge holding capacitor; g) keeping the excitation signal source at the low potential, and turning on the second bias voltage switch to charge the sensing plate to the second bias voltage; h) turning off the second bias voltage switch to leave the sensing plate floating; i) setting the excitation signal source to the high potential; j) charging the second charge holding capacitor to a second output electric potential; k) retaining the second output electric potential by the second charge holding capacitor; and l) producing an output proportional to the difference between the first output electric potential and the second output electric potential by the differential amplifier.

DETAILED DESCRIPTION OF THE PREFERRED EMBODIMENTS

The present invention will now be described more specifically with reference to the following embodiments.

Figure 1:
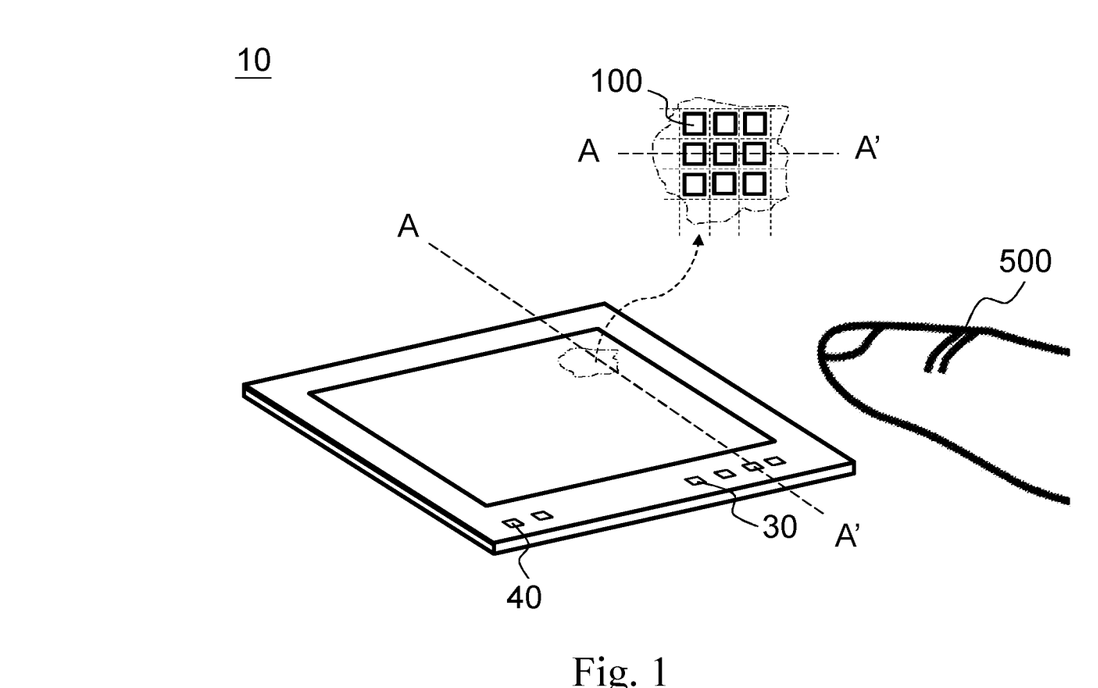
FIG. 1 is a schematic diagram of a capacitive image sensor according to the present invention.

Please see FIG. 1. FIG. 1 shows a schematic diagram of a capacitive image sensor 10 (chip) using capacitive sensing units according to the present invention. The capacitive image sensor 10 is used to depict ridges and valleys of a surface of a finger 500, further converting the results into a noise-reduced image of the fingerprint. The capacitive image sensor 10 includes an array of capacitive sensing units 100, contact pads 40 of a power supply, and contact pads 30 of an input/output (I/O) interface. The output from each capacitive sensing unit 100 represents one corresponding pixel of the fingerprint image.

Figure 2:
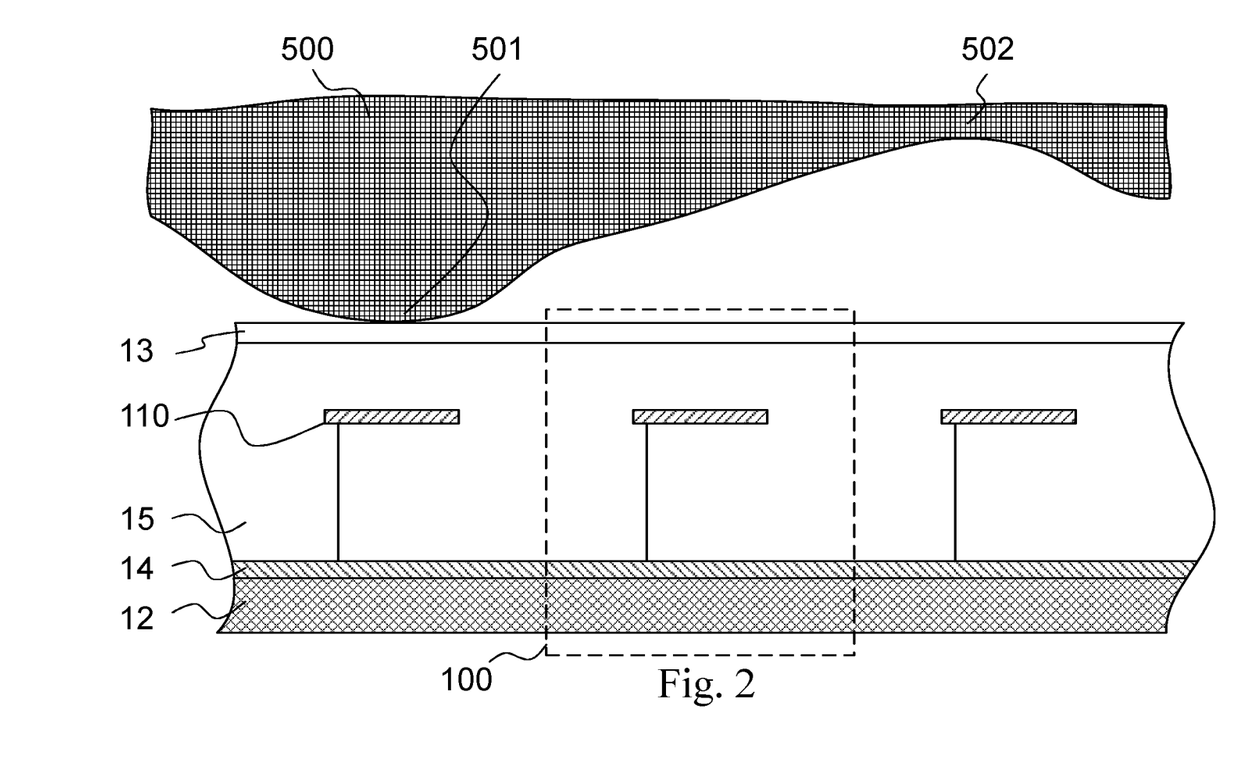
FIG. 2 is a schematic cross-section of a portion of the capacitive image sensor taken along line A-A' in FIG. 1.

FIG. 2 is a schematic cross-section of a portion of the capacitive image sensor 10 taken along line A-A' in FIG. 1, with a protective layer 13 located on top capacitive image sensor 10 and a fingertip 500 placed on the protective layer 13. The protective layer 13 may be made of glass, sapphire, epoxy compound, or coating material. The capacitive image sensor 10 includes a semiconductor substrate 12, having the array of capacitive sensing units 100 formed thereon. The surface of the fingertip 500 includes ridges 501 that are in contact with the protective layer 13 and valleys 502 that are spaced apart from the protective layer 13. Each capacitive sensing unit 100 can be used to transform a distance between a portion of a surface of the approaching finger 500 and a top surface of itself into an output electric potential. Three capacitive sensing units 100 are shown in FIG. 2, and one of the capacitive sensing units 100 is enclosed by a dashed frame. Each capacitive sensing unit 100 includes a sensing plate 110. Below the sensing plates 110 are active semiconductor circuitries 14 schematically shown by a forward-diagonal-lines region in FIG. 2. At least one insulating layer 15 is formed to enclose the sensing plates 110 to insulate the sensing plates 110 from each other. Details of the active semiconductor circuitry 14 will be described in later paragraphs.

Figure 3:
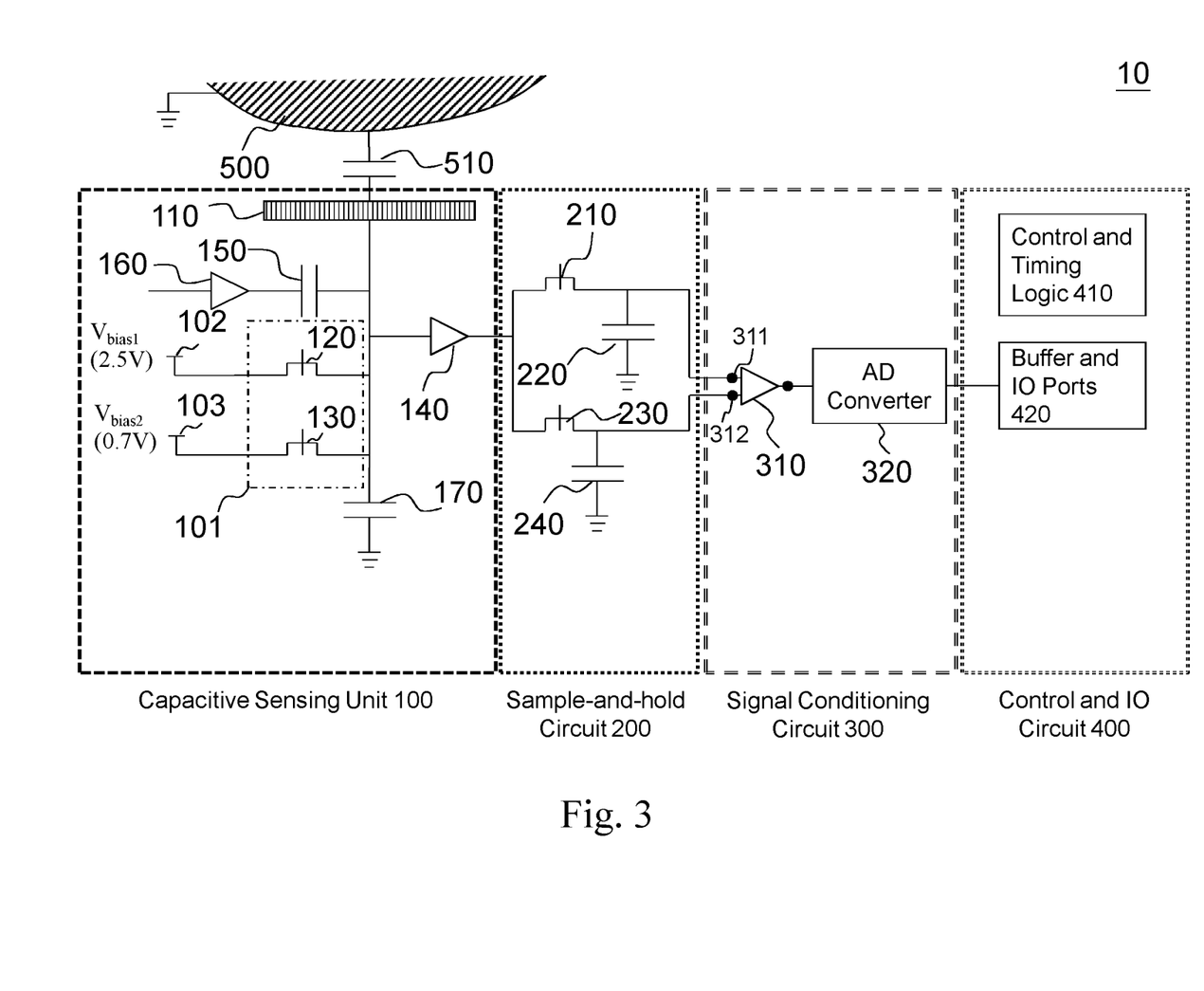
FIG. 3 is an equivalent circuit of a capacitive image sensor with one capacitive sensing unit (one pixel) according to the present invention.

Please refer to FIG. 3. It is an equivalent circuit of the capacitive image sensor 10 with one capacitive sensing unit 100 (one pixel) according to the present invention. The capacitive image sensor 10 includes a capacitive sensing unit 100 (enclosed by a dashed frame), a sample-and-hold circuit 200 (enclosed by a dotted frame), a signal conditioning circuit 300 (enclosed by a double-dashed frame), and a control and IO circuit 400 (enclosed by a double-dotted frame). There should be more capacitive sensing units 100, sample-and-hold circuits 200 and signal conditioning circuits 300 in the capacitive image sensor 10. For a better understanding, only one capacitive sensing unit 100 is used for illustration. Each circuit will be described in detail below.

The capacitive sensing unit 100 is a combination of circuit and metal/insulator structure built to sense small capacitance difference in a small area of a finger 500 to produce a corresponding voltage output. The capacitive sensing unit 100 includes a sensing plate 110, a switch unit 101 (enclosed by a dash-dotted frame), a first bias voltage source 102, a second bias voltage source 103, a voltage follower 140, a reference capacitor 150, and an excitation signal source 160. A parasitic capacitance 170 represents the sum of parasitic capacitance between the sensing plate 110 and other parts of the capacitive sensing unit 100 that are not connected to the sensing plate 110. The value of the parasitic capacitance, denoted as $C_p$, may include the parasitic input capacitance of the voltage follower 140, the drain-to-body capacitance of the switch unit 101, or the stray capacitance of any device with one node connected to the sensing plate 110. When the finger 500 approaches the capacitive sensing unit 100, a finger capacitance 510, denoted as $C_f$, is formed therebetween. The sensing plate 110 is a metal plate at the top side of the capacitive sensing unit 100, used to form one side of a parallel plate capacitor. Here, the parallel plate capacitor is an equivalent capacitor representing the finger capacitance 510. The other side of the parallel plate capacitor is the surface of the finger 500, which is part of the human body. The human body is considered as part of earth ground, or connected to earth ground with low impedance. The switch unit 101 is used to selectively provide the bias voltage to the sensing plate 110. The electric potential of the sensing plate 110 is set to the first bias voltage or the second bias voltage during a resetting stage, and is set floating (i.e. both of the first and second bias voltage supply are removed) during a sensing stage. In the present embodiment, the switch unit 101 may include a first bias voltage switch 120 and a second bias voltage switch 130. The first bias voltage switch 120 is a MOS device connected between the first bias voltage source 102 and the sensing plate 110. The first bias voltage, denoted as $V_{bias1}$, is provided from the first bias voltage source 102 to the sensing plate 110 while the first bias voltage switch 120 is turned on, and stops being provided while the first bias voltage switch 120 is turned off. The first bias voltage is a 2.5V constant voltage reference in the present embodiment. The second bias voltage switch 130 is another MOS device connected between the second bias voltage source 103 and the sensing plate 110. The second bias voltage, denoted as $V_{bias2}$, is provided from the second bias voltage source 103 to the sensing plate 110 while the second bias voltage switch 130 is turned on, and stops being provided while the second bias voltage switch 130 is turned off. The second bias voltage is a 0.7V constant voltage reference in the present embodiment. Multiple capacitive sensing units 100 may share the same first bias voltage source 102 and the same second bias voltage source 103. The voltage follower 140 is a circuit device that has input and output signal. The output signal tracks the input signal. Usually, a voltage follower is implemented as a unity gain amplifier. The input node of the voltage follower 140 is connected to the sensing plate 110, the first bias voltage switch 120, the second bias voltage switch 130 and one end of the reference capacitor 150. It is used to provide sensing results. The excitation signal source 160 is a low-impedance voltage source to provide a bi-level waveform (a positive waveform or a negative waveform) as an excitation signal. The reference capacitor 150 is formed between the excitation signal source 160 and the sensing plate 110, and the reference capacitor 150 is used to inject the excitation signal to the sensing plate 110.

The sample-and-hold circuit 200 in FIG. 3 is a device used to capture and retain input voltage signals. The sample-and-hold circuit 200 includes a first sample switch 210, a first charge holding capacitor 220, a second sample switch 230, and a second charge holding capacitor 240. The first sample switch 210 is formed between the output node of the voltage follower 140 and the first charge holding capacitor 220, and is a MOS device used as a switch to connect the output of the voltage follower 140 to the first charge holding capacitor 220. The first charge holding capacitor 220 is a capacitor used to capture and retain a first output electric potential, denoted as $V_1$, from the voltage follower 140 through the first sample switch 210. One node of the first charge holding capacitor 220 is connected to the first sample switch 210 and the other node is connected to the ground. The second sample switch 230 is formed between the output node of the voltage follower 140 and the second charge holding capacitor 240, and is a MOS device used as a switch to connect the output of the voltage follower 140 to the second charge holding capacitor 240. The second charge holding capacitor 240 is a capacitor used to capture and retain a second output electric potential, denoted as $V_2$, from the voltage follower 140 through the second sample switch 230. One node of the second charge holding capacitor 240 is connected to the second sample switch 230 and the other node is connected to the ground. The first sample switch 210 and the second sample switch 230 work together as a selecting switch for choosing the output target (either the first or the second charge holding capacitor) for the voltage follower 140. In the present embodiment, the sample-and-hold circuit 200 retains at least a first and a second output electric potentials under a corresponding positive waveform or a negative waveform.

The signal conditioning circuit 300 is a circuit to amplify a voltage difference between the first and second output electric potentials, possibly with level shift, and then convert the result to a digitized value. The signal conditioning circuit 300 includes a differential amplifier 310 and an analog-to-digital converter (AD converter) 320. A first input node 311 of the differential amplifier 310 is connected to the first charge holding capacitor 220 and the first sample switch 210, a second input node 312 of the differential amplifier 310 is connected to the second charge holding capacitor 240 and the second sample switch 230, and an output node of the differential amplifier 310 is connected to an input node of the analog-to-digital converter 320. The differential amplifier 310 is an amplifier used to produce a voltage output that is proportional to the difference between the first and second output electric potentials. The analog-to-digital converter 320 converts the output electric potential of the differential amplifier 310 and produces a binary value that represents the voltage level.

The control and TO circuit 400 is a circuit that handles the operation sequence and data input/output of the capacitive image sensor 10. The control and TO circuit 400 includes a control and timing logic 410 and Buffer and TO unit 420. The control and timing logic 410 controls all switches in the capacitive fingerprint sensing device 10. The buffer and TO unit 420 receive the output data of the analog-to-digital converter 320 and store the data into a buffer and then send out the data at a proper time.

Figure 4:
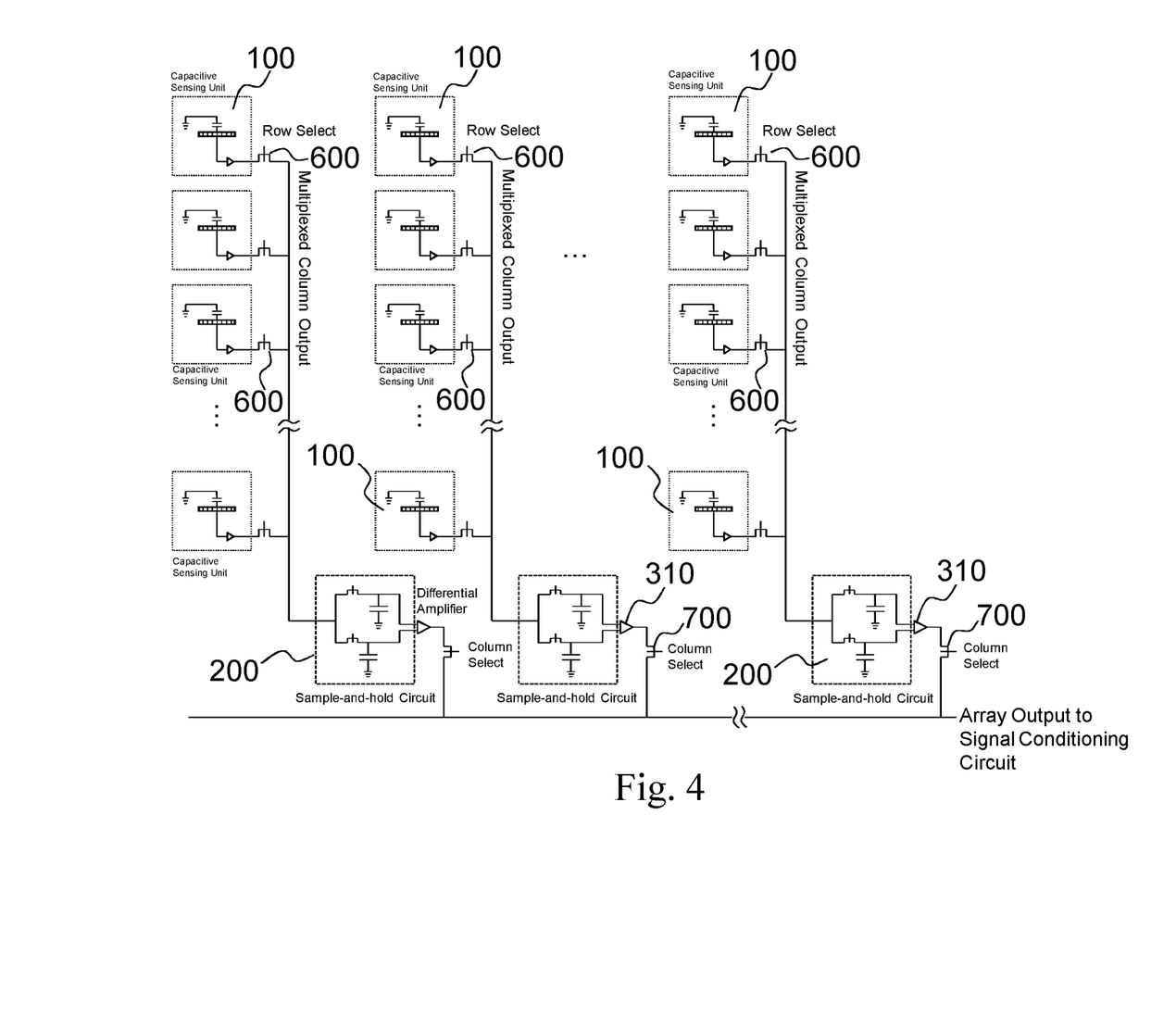
FIG. 4 is a schematic diagram of a typical implementation of the capacitive image sensing device according to the present invention.

Please refer to FIG. 4. FIG. 4 is a schematic diagram of a typical implementation of the capacitive image sensor 10 according to the present invention. The capacitive image sensor 10 includes a two-dimensional array of capacitive sensing units 100 and a number of sample-and-hold circuits 200. Other circuits are not shown in this diagram. The two-dimensional array of the capacitive sensing units 100 is enabled in a row-by-row sequence. The capacitive sensing units 100 in the same column share the same output wire through separate row select signals. One row is enabled by the corresponding row select signal at a time. The row select signal is controlled by the row switches 600. Each column output wire connects to a shared sample-and-hold circuit 200 and a differential amplifier 310. The output of the differential amplifiers 310 is multiplexed to a single output signal through a set of column select signals. The column select signals are controlled by column select switches 700. Only one of the column select signal is activated at a time to allow the output of the differential amplifiers 310 to be sequentially delivered to the analog-to-digital converter 320 in the signal conditioning circuit 300.

Figure 5:
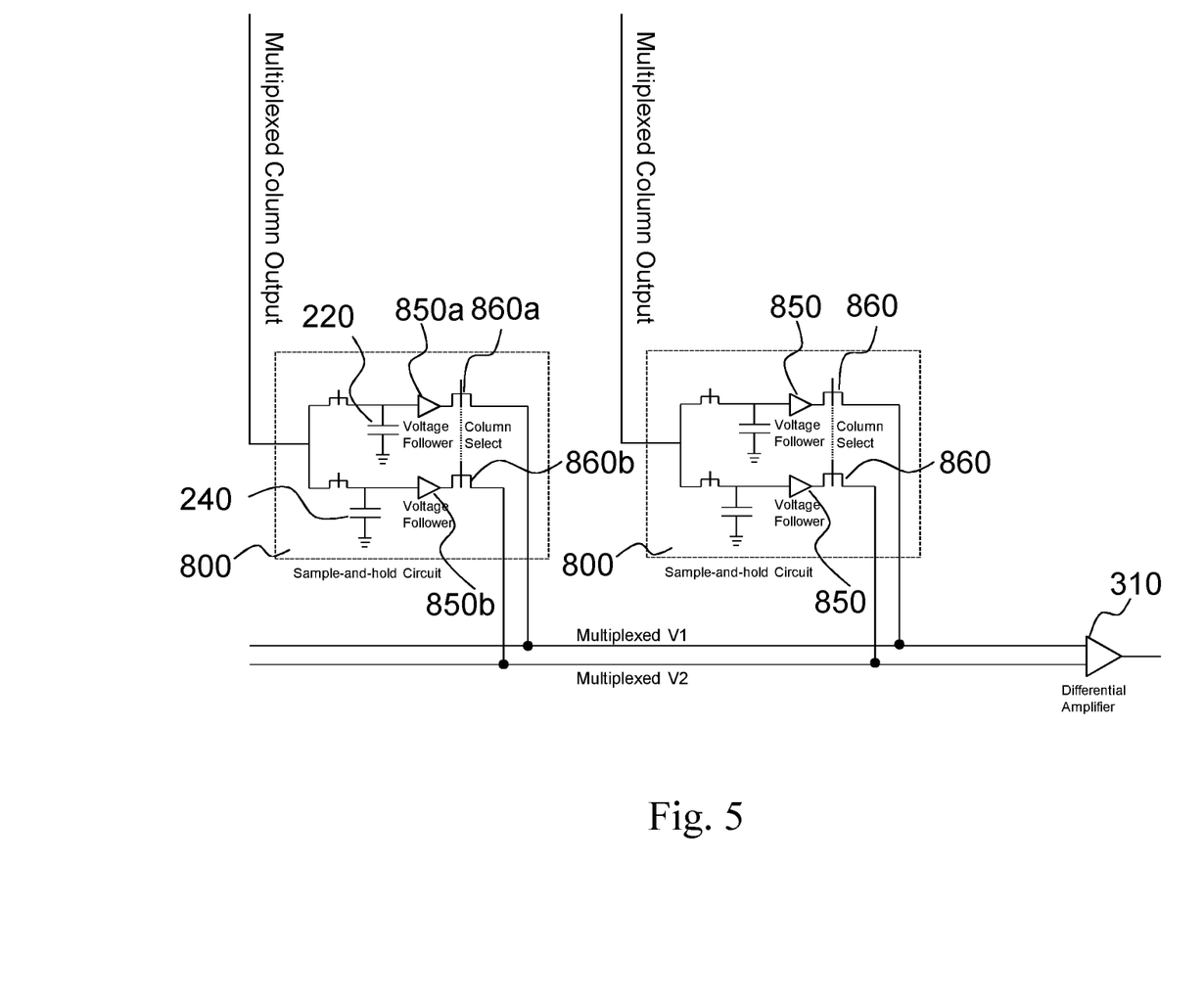
FIG. 5 shows an alternative structure of the sample-and-hold circuit and that of the connection between the differential amplifier and the sample-and-hold circuit.

Please refer to FIG. 5. FIG. 5 shows an alternative structure of a sample-and-hold circuit and that of the connection between the differential amplifier 310 and a sample-and-hold circuit 800. The sample-and-hold circuits 800 may share the same differential amplifier 310 through additional voltage followers 850 and column select switches 860 between the charge holding capacitors and the differential amplifier 310. For example, a voltage follower 850a and a column select switch 860a are formed between the first charge holding capacitor 220 and the differential amplifier 310, and a voltage follower 850b and a column select switch 860b are formed between the second charge holding capacitor 240 and the differential amplifier 310.

Figure 6:
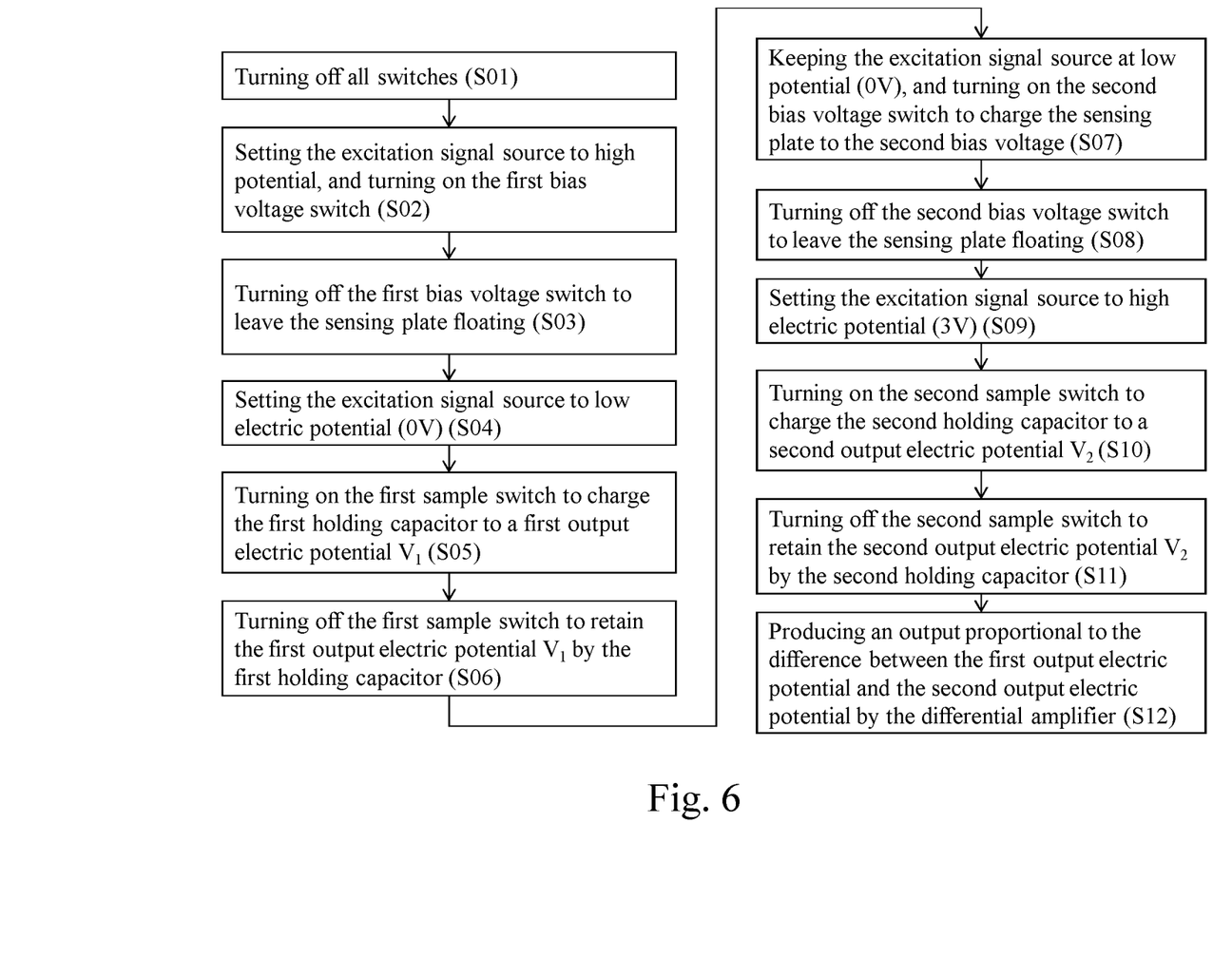
FIG. 6 is a flow chart illustrating a procedure to operate a capacitive sensing unit in the capacitive image sensing device.

A method for operating the capacitive sensing units 100 is also disclosed. Please refer to FIG. 6. It is a flow chart illustrating a procedure to operate a capacitive sensing unit 100 in the capacitive image sensor 10. The steps are:

(S01) at the beginning of the method, turning off all switches, including the first bias voltage switch 120, the second bias voltage switch 130, first sample switch 210, and the second sample switch 220;

(S02) setting the excitation signal source 160 to a high potential (3V), and turning on the first bias voltage switch 120 to charge the sensing plate 110 to the first bias voltage (2.5V);

(S03) turning off the first bias voltage switch 120 to leave the sensing plate 110 floating;

(S04) setting the excitation signal source 160 to a low potential (0V);

(S05) turning on first sample switch 210 to charge the first charge holding capacitor 220 to a first output electric potential $V_1$ that tracks the potential of the sensing plate 110;

(S06) turning off first sample switch 210 to retain the first output electric potential $V_1$ by the first charge holding capacitor 220;

(S07) keeping the excitation signal source 160 at the low potential (0V), and turning on the second bias voltage switch 130 to charge the sensing plate 110 to the second bias voltage (0.7V);

(S08) turning off the second bias voltage switch 130 to leave the sensing plate 110 floating;

(S09) setting the excitation signal source 160 to the high potential (3V);

(S10) turning on the second sample switch 230 to charge the second charge holding capacitor 240 to a second output electric potential $V_2$ that tracks the potential of the sensing plate 110;

(S11) turning off the second sample switch 230 to retain the second output electric potential $V_2$ by the second charge holding capacitor 240; and (S12) producing an output proportional to the difference between the first output electric potential and the second output electric potential by the differential amplifier 310.

The steps S02 to S03 are a first resetting stage. The steps S04 to S06 are a first sensing stage. The first output electric potential corresponding to the first bias voltage and responding to the first voltage change of the excitation signal is retained by the sample-and-hold circuit 200 during the first sensing stage. Namely, a first voltage shift is provided by the excitation signal source 160 to the sensing plate 110 through the reference capacitor 150 during the first sensing stage. The steps S07 to S08 are a second resetting stage. The steps S09 to S11 are a second sensing stage. The second output electric potential corresponding to the second bias voltage and responding to the second voltage change of the excitation signal is retained by the sample-and-hold circuit 200 during the second sensing stage. In other words, a second voltage shift is provided by the excitation signal source 160 to the sensing plate 110 through the reference capacitor 150 during the second sensing stage. In the step S12, the output electric potential of the differential amplifier 310 is the noise-reduced value of that capacitive sensing unit 100 which will be elaborated in detail in later paragraphs. In general, a noise-reduced value of the capacitive sensing unit 100 is obtained by calculating a voltage difference between the first sensing stage and the second sensing stage. There may be additional steps to convert the output electric potentials from the capacitive sensing units 100 into a digitized image. The steps are:

(S13) sequentially collecting the noise-reduced values obtained under corresponding positive waveform and negative waveform for each pixel;

(S14) converting the noise-reduced values into digitized noise-reduced values; and (S15) mapping the digitized noise-reduced values to corresponding locations of capacitive sensing units.

For a better understanding, a result analysis is illustrated below. After the step S04, the potential of the sensing plate 110 should be $$V_{m1} = V_{bias1} + \Delta V_{in1} \cdot \left( \frac{C_r}{C_f + C_r + C_p} \right) = 2.5 - 3 \cdot \left( \frac{C_r}{C_f + C_r + C_p} \right).$$

Here, $C_f$ is a value of the finger capacitance 510, $C_p$ is a value of the parasitic capacitance 170, $C_r$ is a value of the reference capacitor 150, and $\Delta V_{in1}$ is the potential change provided by the excitation signal source. After the step S05, the first output electric potential can be represented by $$V_1 = V_{m1} \cdot G_f + N = G_f \cdot \left\{ V_{bias1} + \Delta V_{in1} \cdot \left( \frac{C_r}{C_f + C_r + C_p} \right) \right\} + N.$$

Here, N is the fixed pattern noise caused by the voltage follower circuit, and $G_f$ is the gain factor of the voltage follower, usually less than 1. After the step S09, the potential of the sensing plate 110 should be $$V_{m2} = V_{bias2} + \Delta V_{in2} \cdot \left( \frac{C_r}{C_f + C_r + C_p} \right) = 0.7 + 3 \cdot \left( \frac{C_r}{C_f + C_r + C_p} \right).$$

After the step S10, the second output electric potential can be represented by $$V_2 = V_{m2} \cdot G_f + N = G_f \cdot \left\{ V_{bias2} + \Delta V_{in2} \cdot \left( \frac{C_r}{C_f + r + C_p} \right) \right\} + N.$$

At the final step S12, the output of the differential amplifier 310 can be represented by $$V_{final} = g \cdot (V_1 - V_2) = g \cdot G_f \cdot \left\{ (V_{bias1} - V_{bias2}) + 2\Delta V \cdot \left( \frac{C_r}{C_f + C_r + C_p} \right) \right\},$$

Since $\Delta V_{in1} = -\Delta V_{in2} = \Delta V$. Here, g is the gain factor of the differential amplifier. The fixed pattern noise term is cancelled in this method.

One may notice that the input voltages to the differential amplifier should be at about the same potential level to avoid unnecessary offset. This requirement can be satisfied by having the design parameter $C_r$ to take the value of $$C_p \cdot \left( \frac{V_{bias1} - V_{bias2}}{2\Delta V - V_{bias1} + V_{bias2}} \right).$$

When this condition is met, we observe that $V_1 = V_2$ when $C_f = 0$.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A noise-reduced capacitive sensing unit, comprising:
   a sensing plate;
   a first bias voltage source, for providing a first bias voltage;
   a second bias voltage source, for providing a second bias voltage;
   a switch unit, connected between two bias voltage sources and the sensing plate, for selectively providing one of the bias voltages to the sensing plate;
   an excitation signal source, for providing an excitation signal with a bi-level waveform;
   a reference capacitor, formed between the excitation signal source and the sensing plate, for injecting the excitation signal to the sensing plate; and
   a voltage follower, for providing sensing results, wherein an input node of the voltage follower is connected to the sensing plate,
   wherein the first bias voltage is provided to the sensing plate during a first resetting stage; the second bias voltage is provided to the sensing plate during a second resetting stage; both of the first and second bias voltages are removed during sensing stages; a first voltage shift is provided by the excitation signal source to the sensing plate through the reference capacitor during a first sensing stage; a second voltage shift is provided by the excitation signal source to the sensing plate through the reference capacitor during a second sensing stage; a noise-reduced value of the capacitive sensing unit is obtained by calculating a voltage difference between the first sensing stage and the second sensing stage.

2. The noise-reduced capacitive sensing unit according to claim 1, further comprising a sample-and-hold circuit for capturing and retaining an input voltage signal, wherein the sample-and-hold circuit comprises:
   a first charge holding capacitor, for capturing and retaining a first output electric potential, wherein one node of the first charge holding capacitor is connected to the ground;
   a second charge holding capacitor, for capturing and retaining a second output electric potential, wherein one node of the second charge holding capacitor is connected to the ground; and
   a selecting switch, for choosing the output target between the first and second charge holding capacitors.

3. The noise-reduced capacitive sensing unit according to claim 2, further comprising a signal conditioning circuit, for amplifying a voltage difference between the first output electric potential and second output electric potential, wherein the signal conditioning circuit comprises:
   a differential amplifier, having a first input node connected to the first charge holding capacitor, and a second input node connected to the second charge holding capacitor, for producing a voltage output that is proportional to the difference between the first output electric potential and second output electric potential.

4. The noise-reduced capacitive sensing unit according to claim 3, further comprising an analog-to-digital converter, having an input node connected to an output node of the differential amplifier, for digitizing an output voltage of the differential amplifier and producing a binary value that represents a level of the output voltage.

5. The noise-reduced capacitive sensing unit according to claim 3, further comprising a control and IO circuit, for handling the operation sequence and data input/output of a capacitive image sensor using the capacitive sensing units, wherein the control and IO circuit comprises:
   a control and timing logic, for controlling all switches of the capacitive sensing unit; and
   a buffer and IO unit, connected to an output node of the analog-to-digital converter, for receiving the output data of the analog-to-digital converter, and store the data into a buffer and then send out the data at a proper time.

6. The noise-reduced capacitive sensing unit according to claim 4, wherein the switch unit comprises:
   a first bias voltage switch, for selectively providing the first bias voltage from the first bias voltage source to the sensing plate; and
   a second bias voltage switch, for selectively providing the second bias voltage from the second bias voltage source to the sensing plate.

7. A capacitive image sensor comprising a plurality of noise-reduced capacitive sensing units according to claim 3.

8. A capacitive image sensor comprising a plurality of noise-reduced capacitive sensing units according to claim 6.

* * * * *